United States Patent
Lipton et al.

(10) Patent No.: US 7,135,548 B2
(45) Date of Patent: *Nov. 14, 2006

(54) MODIFIED α-MSH PEPTIDES AND DERIVATIVES THEREOF

(75) Inventors: James M. Lipton, Woodland Hills, CA (US); Anna P. Catania, Milan (IT)

(73) Assignee: Zengen, Inc., Canoga Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/882,085

(22) Filed: Jun. 29, 2004

(65) Prior Publication Data

US 2005/0130901 A1  Jun. 16, 2005

Related U.S. Application Data

(63) Continuation-in-part of application No. 10/714,343, filed on Nov. 14, 2003.

(60) Provisional application No. 60/426,929, filed on Nov. 14, 2002.

(51) Int. Cl.
*A61K 38/08* (2006.01)
*C07K 7/06* (2006.01)

(52) U.S. Cl. .................... 530/328; 514/16; 530/312

(58) Field of Classification Search .................. None
See application file for complete search history.

(56) References Cited

U.S. PATENT DOCUMENTS 6,780,838 B1 * 8/2004 Lipton et al. .................. 514/2
6,887,846 B1 * 5/2005 Catania et al. ................. 514/2
6,939,846 B1 * 9/2005 Lipton et al. .................. 514/2

FOREIGN PATENT DOCUMENTS

WO  WO 00/59527 A1 * 10/2000

OTHER PUBLICATIONS

Grieco et al. Novel alpha-Melanocyte Stimulating Hormone Peptide Analogues with High Candidacidal Activity. Journal of Medicinal Chemistry. Jan. 30, 2003, vol. 46, No. 5, pp. 850-855.*
Sawyer et al. Structure-Activity Relationships of Nle4,DPhe7 alpha-MSH. Annals of the New York Academy of Sciences. 1993, vol. 680, pp. 597-599.*

* cited by examiner

*Primary Examiner*—Jeffrey Edwin Russel
(74) *Attorney, Agent, or Firm*—Dykema Gossett PLLC; Gregory M. Zinkl

(57) ABSTRACT

Novel peptides with antimicrobial activity are disclosed. The novel peptides are octomeric peptides modified from α-MSH. The modified α-MSH antimicrobial peptides disclosed herein may have enhanced activity against microbes over α-MSH due to modifications in peptide sequence and chirality of amino acids. Due an identified mechanism of action for antimicrobial activity in which cAMP accumulates in the microbial cell, it may be that microbes will not generate resistance to these modified α-MSH antimicrobial peptides.

14 Claims, No Drawings

SEQUENCE LISTING

<160> NUMBER OF SEQ ID NOS: 46

<210> SEQ ID NO 1
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (7)..(7)
<223> OTHER INFORMATION: Where X is Phe or DPhe and where Val is the
      carboxy-terminal amino acid

<400> SEQUENCE: 1

His Phe Arg Trp Gly Lys Xaa Val
1               5

<210> SEQ ID NO 2
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DPhe or DNal

<400> SEQUENCE: 2

His Xaa Arg Trp Gly Lys Pro Val
1               5

<210> SEQ ID NO 3
<211> LENGTH: 8

```
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(7)
<223> OTHER INFORMATION: Where X at position 2 is DPhe or DNal and X at
      position 7 is Phe or DPhe and Val is the carboxy-terminal
      amino acid

<400> SEQUENCE: 3

His Xaa Arg Trp Gly Lys Xaa Val
1               5

<210> SEQ ID NO 4
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (7)..(7)
<223> OTHER INFORMATION: Where X is an amino acid having a non-polar fun
      ctional group and where Val is the carboxy-terminal
      amino acid

<400> SEQUENCE: 4

His Phe Arg Trp Gly Lys Xaa Val
1               5

<210> SEQ ID NO 5
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (8)..(8)
<223> OTHER INFORMATION: Where X is the carboxy-terminal amino acid
      and where X is an amino acid, not including Val, having a non-polar
      functional group or  a hydrophobic functional group

<400> SEQUENCE: 5

His Phe Arg Trp Gly Lys Pro Xaa
1               5

<210> SEQ ID NO 6
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (6)..(6)
<223> OTHER INFORMATION: Where X is an amino acid, not including Lys,
      having a non-polar functional group and where Val is the
      carboxy-terminal amino acid

<400> SEQUENCE: 6

His Phe Arg Trp Gly Xaa Pro Val
1               5

<210> SEQ ID NO 7
<211> LENGTH: 8
<212> TYPE: PRT
<213> ORGANISM: Artificial Sequence
<220> FEATURE:
```

```
<223> OTHER INFORMATION: Synthesized polypeptide
<220> FEATURE:
<221> NAME/KEY: misc_feature
<222> LOCATION: (7)..(7)
<223> OTHER INFORMATION: Where X is an amino acid with a positively
      charged functional group and where Val is the
      carboxy-terminalamino acid

<400> SEQUENCE: 7

His Phe Arg Trp Gly Lys Xaa Val
1               5

<210> SEQ ID NO 8
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (7)..(7)
<223> OTHER INFORMATION: Where X is an amino acid having a negatively
      charged functional group and where Val is the
      carboxy-terminal amino acid

<400> SEQUENCE: 8

His Phe Arg Trp Gly Lys Xaa Val
1               5

<210> SEQ ID NO 9
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(7)
<223> OTHER INFORMATION: Where X at position 2 is DPhe or DNal and X at
      position 7 is an amino acid having a negatively charged
      functional group

<400> SEQUENCE: 9

His Xaa Arg Trp Gly Lys Xaa Val
1               5

<210> SEQ ID NO 10
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (4)..(4)
<223> OTHER INFORMATION: Where X is DTrp and Val is the carboxy-terminal
      amino acid

<400> SEQUENCE: 10

His Phe Arg Xaa Gly Lys Pro Val
1               5

<210> SEQ ID NO 11
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (7)..(7)
```

<223> OTHER INFORMATION: Where X is an amino acid having an uncharged
      polar functional group and where Val is the carboxy-terminal
      amino acid

<400> SEQUENCE: 11

His Phe Arg Trp Gly Lys Xaa Val
1               5

<210> SEQ ID NO 12
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(7)
<223> OTHER INFORMATION: Where X at position 2 is DPhe or DNal and X at
      position 7 is an amino acid with uncharged functional group and
      where Val is the carboxy-terminal amino acid

<400> SEQUENCE: 12

His Xaa Arg Trp Gly Lys Xaa Val
1               5

<210> SEQ ID NO 13
<211> LENGTH: 13
<212> TYPE: PRT
<213> ORGANISM: Artificial Sequence
<220> FEATURE:
<223> OTHER INFORMATION: Synthesized polypeptide

<400> SEQUENCE: 13

Ser Tyr Ser Met Glu His Phe Arg Trp Gly Lys Pro Val
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthesized polypeptide

<400> SEQUENCE: 14

Met Glu His Phe Arg Trp Gly
1               5

<210> SEQ ID NO 15
<211> LENGTH: 3
<212> TYPE: PRT
<213> ORGANISM: Artificial Sequence
<220> FEATURE:
<223> OTHER INFORMATION: Synthesized polypeptide

<400> SEQUENCE: 15

Lys Pro Val
1

<210> SEQ ID NO 16
<211> LENGTH: 4
<212> TYPE: PRT
<213> ORGANISM: Artificial Sequence
<220> FEATURE:
<223> OTHER INFORMATION: Synthesized polypeptide

<400> SEQUENCE: 16

His Phe Arg Trp
1

<210> SEQ ID NO 17
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (8)..(8)
<223> OTHER INFORMATION: Where X at position 8 is DVal

<400> SEQUENCE: 17

His Phe Arg Trp Gly Lys Pro Xaa
1               5

<210> SEQ ID NO 18
<211> LENGTH: 8
<212> TYPE: PRT
<213> ORGANISM: Artificial Sequence
<220> FEATURE:
<223> OTHER INFORMATION: Synthesized polypeptide

<400> SEQUENCE: 18

His Phe Arg Trp Gly Ala Pro Val
1               5

<210> SEQ ID NO 19
<211> LENGTH: 8
<212> TYPE: PRT
<213> ORGANISM: Artificial Sequence
<220> FEATURE:
<223> OTHER INFORMATION: Synthesized polypeptide

<400> SEQUENCE: 19

His Phe Arg Trp Gly Lys Ala Val
1               5

<210> SEQ ID NO 20
<211> LENGTH: 8
<212> TYPE: PRT
<213> ORGANISM: Artificial Sequence
<220> FEATURE:
<223> OTHER INFORMATION: Synthesized polypeptide

<400> SEQUENCE: 20

His Phe Arg Trp Gly Lys Pro Ala
1               5

<210> SEQ ID NO 21
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DPhe

<400> SEQUENCE: 21

His Xaa Arg Trp Gly Lys Pro Val
1               5

<210> SEQ ID NO 22
<211> LENGTH: 8
<212> TYPE: PRT
<213> ORGANISM: Artificial Sequence

```
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DNal

<400> SEQUENCE: 22

His Xaa Arg Trp Gly Lys Pro Val
1               5

<210> SEQ ID NO 23
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (4)..(4)
<223> OTHER INFORMATION: Where X is DTrp

<400> SEQUENCE: 23

His Phe Arg Xaa Gly Lys Pro Val
1               5

<210> SEQ ID NO 24
<211> LENGTH: 8
<212> TYPE: PRT
<213> ORGANISM: Artificial Sequence
<220> FEATURE:
<223> OTHER INFORMATION: Synthesized polypeptide

<400> SEQUENCE: 24

His Phe Arg Trp Gly Lys Pro Leu
1               5

<210> SEQ ID NO 25
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (7)..(7)
<223> OTHER INFORMATION: Where X is DAla

<400> SEQUENCE: 25

His Phe Arg Trp Gly Lys Xaa Val
1               5

<210> SEQ ID NO 26
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DNal

<400> SEQUENCE: 26

His Xaa Arg Trp Gly Lys Ala Val
1               5

<210> SEQ ID NO 27
<211> LENGTH: 8
```

```
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(7)
<223> OTHER INFORMATION: Where X at position 2 is DNal and X at position
      7 is DAla

<400> SEQUENCE: 27

His Xaa Arg Trp Gly Lys Xaa Val
1               5

<210> SEQ ID NO 28
<211> LENGTH: 8
<212> TYPE: PRT
<213> ORGANISM: Artificial Sequence
<220> FEATURE:
<223> OTHER INFORMATION: Synthesized polypeptide

<400> SEQUENCE: 28

His Phe Arg Trp Gly Lys Gly Val
1               5

<210> SEQ ID NO 29
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DNal

<400> SEQUENCE: 29

His Xaa Arg Trp Gly Lys Gly Val
1               5

<210> SEQ ID NO 30
<211> LENGTH: 8
<212> TYPE: PRT
<213> ORGANISM: Artificial Sequence
<220> FEATURE:
<223> OTHER INFORMATION: Synthesized polypeptide

<400> SEQUENCE: 30

His Phe Arg Trp Gly Lys Ser Val
1               5

<210> SEQ ID NO 31
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DNal

<400> SEQUENCE: 31

His Xaa Arg Trp Gly Lys Ser Val
1               5

<210> SEQ ID NO 32
<211> LENGTH: 8
<212> TYPE: PRT
```

```
<213> ORGANISM: Artificial Sequence
<220> FEATURE:
<223> OTHER INFORMATION: Synthesized polypeptide

<400> SEQUENCE: 32

His Phe Arg Trp Gly Lys Phe Val
1               5

<210> SEQ ID NO 33
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (7)..(7)
<223> OTHER INFORMATION: Where X is DPhe

<400> SEQUENCE: 33

His Phe Arg Trp Gly Lys Xaa Val
1               5

<210> SEQ ID NO 34
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DPhe

<400> SEQUENCE: 34

His Xaa Arg Trp Gly Lys Phe Val
1               5

<210> SEQ ID NO 35
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(7)
<223> OTHER INFORMATION: Where X at position 2 is DPhe and X at position
      7 is DPhe

<400> SEQUENCE: 35

His Xaa Arg Trp Gly Lys Xaa Val
1               5

<210> SEQ ID NO 36
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DNal

<400> SEQUENCE: 36

His Xaa Arg Trp Gly Lys Phe Val
1               5
```

```
<210> SEQ ID NO 37
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(7)
<223> OTHER INFORMATION: Where X at position 2 is DNal and X at position
      7 is DPhe

<400> SEQUENCE: 37

His Xaa Arg Trp Gly Lys Xaa Val
1               5

<210> SEQ ID NO 38
<211> LENGTH: 8
<212> TYPE: PRT
<213> ORGANISM: Artificial Sequence
<220> FEATURE:
<223> OTHER INFORMATION: Synthesized polypeptide

<400> SEQUENCE: 38

His Phe Arg Trp Gly Lys Asp Val
1               5

<210> SEQ ID NO 39
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (7)..(7)
<223> OTHER INFORMATION: Where X is DAsp

<400> SEQUENCE: 39

His Phe Arg Trp Gly Lys Xaa Val
1               5

<210> SEQ ID NO 40
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DPhe

<400> SEQUENCE: 40

His Xaa Arg Trp Gly Lys Asp Val
1               5

<210> SEQ ID NO 41
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DNal

<400> SEQUENCE: 41

His Xaa Arg Trp Gly Lys Asp Val
```

```
<210> SEQ ID NO 42
<211> LENGTH: 8
<212> TYPE: PRT
<213> ORGANISM: Artificial Sequence
<220> FEATURE:
<223> OTHER INFORMATION: Synthesized polypeptide

<400> SEQUENCE: 42

His Phe Arg Trp Gly Lys Glu Val
1               5

<210> SEQ ID NO 43
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DNal

<400> SEQUENCE: 43

His Xaa Arg Trp Gly Lys Glu Val
1               5

<210> SEQ ID NO 44
<211> LENGTH: 8
<212> TYPE: PRT
<213> ORGANISM: Artificial Sequence
<220> FEATURE:
<223> OTHER INFORMATION: Synthesized polypeptide

<400> SEQUENCE: 44

His Phe Arg Trp Gly Lys Lys Val
1               5

<210> SEQ ID NO 45
<211> LENGTH: 8
<212> TYPE: PRT
<213> ORGANISM: Artificial Sequence
<220> FEATURE:
<223> OTHER INFORMATION: Synthesized polypeptide
<220> FEATURE:
<221> NAME/KEY: misc_feature
<222> LOCATION: (2)..(2)
<223> OTHER INFORMATION: Where X is DNal

<400> SEQUENCE: 45

His Xaa Arg Trp Gly Lys Lys Val
1               5

<210> SEQ ID NO 46
<211> LENGTH: 39
<212> TYPE: PRT
<213> ORGANISM: Homo sapiens

<400> SEQUENCE: 46

Ser Tyr Ser Met Glu His Phe Arg Trp Gly Lys Pro Val Gly Lys Lys
1               5                   10                  15

Arg Arg Pro Val Lys Val Tyr Pro Ala Gly Gln Asp Asp Gln Ala Ser
            20                  25                  30

Gln Ala Phe Pro Leu Gln Phe
            35
```

MODIFIED α-MSH PEPTIDES AND DERIVATIVES THEREOF

PRIORITY CLAIM

This application is a Continuation-in-Part of U.S. patent application Ser. No. 10/714,343, filed Nov. 14, 2003, now pending, which claims priority to U.S. Provisional Application Ser. No. 60/426,929, filed Nov. 14, 2002, both of which are incorporated herein by reference.

BACKGROUND OF THE INVENTION

Antibiotics, and in general, antimicrobials, have been in commercial use for decades. Antimicrobials have played an enormous role in both enhancing quality of life and extending life expectancy.

Despite their effectiveness in fighting infection, antimicrobial agents have some well-known drawbacks. First, they can eliminate significant numbers of mutually beneficial native flora, opening the door for opportunistic infection. In other words, the successful treatment of unwanted bacteria or other microorganism may kill enough mutually beneficial microorganisms to allow an opportunistic pathogen to increase numbers to a pathogenic level.

For example, humans have over 400 species of commensal bacteria, present mostly in the colon and ileum, whose existence is essential to normal digestion by humans. Intestinal bacteria alone collectively weigh as much as one kilogram and number approximately $10^{14}$. Yet, humans manage to cohabit with the intestinal flora in a mutually beneficial symbiotic relationship. Centers for Disease Control: "*Campaign to Prevent Antimicrobial Resistance in Healthcare Settings,*" 2002. Mutually beneficial gut flora compete with pathogenic species for space and nutrients, usually preventing pathogenic colonization. Similarly, mutually beneficial bacteria, if allowed to grow unchecked, may themselves become pathogenic.

On the other hand, an antibiotic that kills large numbers of mutually beneficial bacteria may eliminate competition for pathogenic bacteria, providing them with space and nutrients that otherwise would be unavailable to them. One example is the opportunistic pathogen is *Clostridium difficile*. Typically, *C. difficile* is not present at pathogenic levels in the intestine. If, certain mutually beneficial intestinal bacteria are eliminated after intense or prolonged antibiotic exposure, *C. difficile* will begin to colonize the intestine in large numbers, resulting in a significant infection capable of producing toxins that result in inflammation and injury to the intestinal lining. This colonization is allowed as a result of the lack of other bacteria, bacteria whose existence would have checked the growth of *C. difficile*, that have been eliminated by the long term antibiotic treatment.

Another common example is seen in the treatment of any number of infections in women. Infectious conditions, upper respiratory infections or urinary tract infections for example, treated with antibiotics may lead to other complications. Often times, women treated with broad spectrum antibiotics for a variety of bacterial infections often develop vaginal yeast infections due to the wiping out of the natural flora of the vagina, a flora that normally keep yeast, *Candida albicans* specifically, in check. A natural antibiotic treatment that does not disrupt the balance of the normal flora is needed.

The normal flora is easily distinguished from pathogenic bacteria, as are normal flora that have mounted an opportunistic infection. Antibiotics are created to selectively kill a certain group of bacteria, Gram positive for example. Upon the discovery and development of a new antimicrobial, an antimicrobial's spectrum of action is easily determined by using well-established techniques. The Kirby-Bauer Disc Diffusion test is one such technique. Microbes are grown in agar plates containing paper discs coated with the antimicrobial agent. By measuring the diameter of growth inhibition around the disc, one can determine which strains are susceptible or resistant to the antimicrobial agent. Discs with larger diameters of inhibition indicate that the strain is susceptible to the antimicrobial agent, and likely will be easily treated in a patient setting. Discs with smaller diameters of inhibition surrounding them are indicative of the presence of more resistant microbes that may take longer to kill in a patient. Those with no diameter of inhibition indicate that the microbes either already harbor resistant genes or have mutated to become resistant. As resistant bacteria propagate, the genes responsible for their resistance will be passed to successive generations. If resistant bacteria establish an infection in a patient, the results can be devastating.

Antimicrobial resistance has been recognized since the introduction of penicillin nearly 50 years ago when patients having penicillin-resistant *S. aureus* infections appeared. As early as 1946, only 3 years after companies began mass-producing penicillin, a London hospital reported that 14% of *S. aureus* strains taken from patients were penicillin-resistant. Drexler, M., "*Secret Agents: The Menace of Emerging Infections,*" Joseph Henry Press, 2002. Today, hospitals worldwide are facing infection control problems from the rapid emergence and dissemination of other microbes resistant to one or more antimicrobial agents.

Microbes, regardless of their resistance status, are normally recognized and ablated by an individual's immune system. If, however, the microbe population is sufficiently large and their growth outpaces the immune system's ability to eliminate them, an infection can result that may threaten the health of the individual. Treatment with an antimicrobial agent will eliminate a large percentage of the pathogenic microbial population in a patient, which allows the patient's immune system to ablate the remaining pathogenic organisms. In contrast, resistant microbes do not succumb to antibiotic therapy and if the immune system is unable to eliminate them, their colonization may result in persistent infections that are difficult, if not impossible, to treat using currently available therapies.

Prolonged antibiotic exposure, among other causes, may also result in "super infection." Super infection is best understood with reference to basic Darwinian theory. Those microbes whose phenotype presents more resistance to certain antimicrobials will result in the proliferation of similar bacteria who are "selected in" by the antimicrobial. Essentially, the more sensitive bacteria are killed while the more resistant survive and thrive. Antimicrobials are designed to kill off sensitive bacteria, bacteria that have proliferated for any number of reasons, beyond the body's cellular and humoral based immunity systems' ability to overcome the infection. Usually, the number of sensitive bacteria significantly outnumber the resistant strains. Antimicrobial therapy directed to a specific microbe, in addition to the body's immune system, has been successful in clearing infection. However, long term administrations of an antibiotic treatment, osteomylitis for example, may result in the killing of all sensitive bacteria but no resistant bacteria. In this case, if the proliferation of resistant bacteria overcomes the body's natural ability to control the rate of growth of the resistant bacteria, a super infection of resistant bacteria develops.

In a nearly opposite situation, that of uncompleted antimicrobial treatment, a similar resultant super infection is possible. Antibiotic therapy is designed to last beyond the period of symptomatic treatment. In other words, the medications are to be taken beyond that point a patient no longer experiences symptoms of the infection. When treatment is aborted prior to a full "course of antibiotics," a super infection may result. The early portion of a normal course of antibiotic treatment usually results in the killing of the majority of sensitive bacteria. The remaining course of antibiotics keeps the remaining bacteria in check while the body fights the remaining sensitive bacteria and the rare population of resistant bacteria, a population that may not exist in every patient. In those cases where a patient may contain a population of resistant bacteria, the uncompleted course of antibiotic treatment may result in a proliferation of resistant bacteria beyond the body's natural ability to fight infection. Essentially, the incomplete course kills the weakest bacteria leaving the strong to survive. In Darwinian terms, the resistant bacteria have been selected in. As more and more hosts select in more and more resistant strains of bacteria, these bacteria become predominant and new medications are needed to combat them. A treatment that poses less of a risk of creating resistant strains of bacteria is needed.

Resistant microbes represent a major concern to the medical community. More than an estimated $30 billion was spent in 2000 alone treating antimicrobial-resistant infections. "*Antimicrobial Resistance*," Office of Communications and Public Liaison, National Institute of Allergy and Infectious Diseases, National, Bethesda, Md., June 2000. Standard therapies for treating infections become more limited in the face of antimicrobial-resistant bacteria, increasing the risk of serious, untreatable, sometimes life-threatening infections. Drug-resistant pathogens are a growing threat and are troublesome in healthcare settings. Nearly 2 million patients contract hospital-acquired infections, or "nosocomial" infections, every year in the United States alone, and about 90,000 die as a result of their infection. Centers for Disease Control: "*Campaign to Prevent Antimicrobial Resistance in Healthcare Settings*," 2002. More than 70% of the bacteria that cause hospital-acquired infections are resistant to at least one of the drugs commonly used to treat them. Persons infected with drug-resistant organisms are more likely to have longer hospital stays and/or require treatment with second or third-choice drugs that may be less effective, more toxic, and/or more expensive.

A recent and publicized example of this phenomenon occurred with the drug ciprofloxicin and the bacteria, *Psudomonas aeriginosa*. *P. aeriginosa* is a Gram negative bacteria that is resistant to many antimicrobials. It has been especially difficult to treat in patients with diabetic infections, which commonly lead to gangrene, amputation and death. The drug was used as specific therapy for patients having a *P. aeriginosa* infection and for broad spectrum treatment in cases where the pathogen had not been identified. The drug was successful at treating infection and doctors across the country began using the medication as a broad-spectrum therapy, especially in the common cases of upper respiratory infection. In time, ciprofloxicin-resistant strains of *P. aeriginosa* emerged. An infection with these resistant bacteria posed a risk to the patient and an increased difficulty of treatment for the physician. This problem is now difficult in an immunocompromised patient.

A similar example involves another genus of bacteria common to humans. Staphylococci are a type of Gram positive bacteria normally present in skin and mucosal membranes of the body. *S. aureus*, in particular, is a virulent opportunistic pathogen that causes many skin, bone, mucous membrane infections, bacterial endocarditis, respiratory infection, food poisoning and toxic shock syndrome, to name only a few. *S. aureus* infections were commonly treated with the methicillin, a member of the penicillin class of antibiotics. This was the treatment of choice before beta lactamase inhibitor antibiotics, clavulanic acid for example, became available. Although methicillin was effective against "Staph" infections, some *S. aureus* strains developed resistance to it, and only a few antibiotics were available to successfully treat methicillin-resistant *Staphylococcus aureus* (MRSA). One such antibiotic commonly used to treat MRSA infection is vancomycin. A strain of *S. aureus*, however, with reduced susceptibility to vancomycin (VISA) has already been identified. Khurshid, M. A., et. al., *Staphylococcus aureus with Reduced Susceptibility to Vancomycin*—Illinois, 1999, Morbidity and Mortality Weekly Report, 48(51): 1165–1167 (2000). Strains of *S. aureus* resistant to methicillin and other antibiotics are endemic in hospitals. Infection with methicillin-resistant MRSA strains may also be increasing in non-hospital settings. Increasing reliance on vancomycin has led to the emergence of vancomycin-resistant enterococci (VRE), bacteria that infect wounds, the urinary tract and other sites. Until 1989, such resistance had not been reported in U.S. hospitals. By 1993, however, more than 10 percent of hospital-acquired enterococci infections reported to the CDC were resistant. Nordenberg, T., *Miracle Drugs Versus Superbugs*, FDA Consumer Article, November-December 1998.

*Streptococcus pneumoniae* is another pathogenic bacteria. It causes thousands of cases of meningitis and pneumonia, and 7 million cases of ear infection in the United States each year. Currently, about 30 percent of *S. pneumoniae* isolates are resistant to penicillin, the primary drug used to treat this infection. Many penicillin-resistant strains are also resistant to other antimicrobial drugs. "*Antimicrobial Resistance,*" Office of Communications and Public Liaison, National Institute of Allergy and Infectious Diseases, National, Bethesda, Md., June 2000.

In sexually transmitted disease clinics that monitor outbreaks of drug-resistant infections, doctors have found that more than a third of gonorrhea isolates are resistant to penicillin, tetracycline, or both. "*Sexually Transmitted Disease Surveillance 1997*" Division of STD Prevention, September 1998, U.S. Department of Health and Human Services, Public Health Service, Centers for Disease Control and Prevention, National Center for HIV, STD, and TB Prevention, Division of STD Prevention, Atlanta, Ga.

Strains of multi-drug-resistant tuberculosis (MDR-TB) have also emerged over the last decade and pose a particular threat to people infected with HIV. MDR-TB strains are just as contagious as TB strains that are drug-sensitive. MDR-TB is more difficult and vastly more expensive to treat, and patients may remain infectious longer due to inadequate treatment, thereby increasing the likelihood of transmission. "*Antimicrobial Resistance*," Office of Communications and Public Liaison, National Institute of Allergy and Infectious Diseases, National, Bethesda, Md., June 2000.

Diarrheal diseases cause almost 3 million deaths a year, mostly in developing countries, where resistant strains of highly pathogenic bacteria such as *Shigella dysenteriae, Campylobacter, Vibrio cholerae, Escherichia coli* and *Salmonella* are emerging. Recent outbreaks of *Salmonella* food poisoning have occurred in the United States. A potentially dangerous "superbug" known as *Salmonella typhimurium*, resistant to ampicillin, sulfa, streptomycin, tetracycline and chloramphenicol, has caused illness in Europe, Canada and the United States. "*Antimicrobial Resistance*," Office of Communications and Public Liaison, National Institute of Allergy and Infectious Diseases, National, Bethesda, Md., June 2000.

Fungal pathogens account for a growing proportion of nosocomial, or hospital acquired, infections. Fungal diseases such as candidiasis and *Pneumocystis carinii* pneumonia are common among AIDS patients, and isolated outbreaks of other fungal diseases in people with normal immune systems have occurred recently in the United States. Scientists and clinicians are concerned that the increasing use of antifungal drugs will lead to drug-resistant fungi. In fact, recent studies have documented resistance of *Candida* species to fluconazole, a drug used widely to treat patients with systemic fungal diseases. "*Antimicrobial Resistance*," Office of Communications and Public Liaison, National Institute of Allergy and Infectious Diseases, National, Bethesda, Md., June 2000. Moreover, recently isolated *C. albicans* strains from patients have exhibited resistance to amphotericin B, which is currently the only antifungal agent from the class of approximately 200 known polyene agents safe enough for intravenous administration. Ellis, D., "*Amphotericin B: Spectrum and Resistance*," Journal of Antimicrobial Chemotherapy 49 Supp 1: 7–10, 2002.

In recent years, the emergence of resistant strains to commonly used antimicrobials has stimulated a search for new, and naturally occurring, antimicrobial compounds having clinical utility. Thus, a new and natural medication is needed that uniformly attacks bacteria that are both sensitive and resistant to classical medicines. Further, the new medication should be equipotent across genera of bacteria to help, as closely as possible, the immune system to maintain the intricate balance of the body's natural flora.

Certain endogenous peptides have shown antimicrobial activity against bacteria, fungi and enveloped viruses but with little or no cytolytic activity, have been isolated from diverse sources. Martin, E et al, "*Defensins and other endogenous peptide antibiotics of vertebrates*," J. of Leukocyte Biology 58: 128–36, 1995. Most of these peptides share the property of being cationic but they differ considerably in some features, such as their size, the presence of disulfide bonds and structural motifs. Gabay, J., "*Ubiquitous Natural Antibiotics*," Science 264:373–4, 1994. These peptides have been shown to exert their antimicrobial activities either by forming multimeric pores in the lipid bilayer of the cell membrane or through interacting with macromolecular synthesis after penetration into the cell membrane. Zasloff, M., "*Antibiotic peptides as mediators of innate immunity*," Current Opinions in Immunology 4: 3, 1992; see also Boman, H. et al, "*Mechanisms of action on Escherichia coli of cecropin P1 and PR-39, two antibacterial peptides from pig intestine*," Infection and Immunity 61: 2978–84, 1993. The most important aspect of antimicrobial peptides is that they rarely induce bacterial resistance. Oren, Z., et al, "*A class of highly potent antibacterial peptides derived from pardaxin, a pore-forming peptide isolated from Moses sole fish Pardachirus marmoratus*," European Journal of Biochemistry 237, 303–10, 1996. Accordingly, antimicrobial peptides are promising candidates in the continuing search for a new class of antibiotics. It is an object of this invention to create antimicrobial peptides for use in antimicrobial treatments.

SUMMARY OF THE INVENTION

The current invention is directed to α-MSH-related peptides. More specifically, the alpha-MSH peptides have been structurally modified from alpha-MSH. These modified alpha MSH peptides are contemplated for use in antimicrobial therapy to treat infections. The modified α-MSH peptides maintain advantages over other antimicrobial therapy in that they are less likely to generate resistant microbial strains and are virtually non-toxic to mammalian cells. Infections can include those of bacterial, viral, parasitic and fungal origin.

The α-isoform of melanocyte-stimulating hormone (MSH) (SEQ. ID. NO. 13) is a naturally occurring 13-amino acid peptide. α-MSH (SEQ. ID. NO. 13) and its carboxy-terminal tripeptide, Lys-Pro-Val (SEQ. ID. NO. 15), each have potent anti-inflammatory properties and have exhibited antimicrobial properties toward two representative classes of organisms, fungus and bacteria: *S. Aureus* and *Candida Albicans*, respectively. Catania, A, et al., "*Antimicrobial Effects of α-MSH Peptides*," Journal of Leukocyte Biology 67: 233–239, 2000; see also, Catania, A., et al., "*Anti-Inflammatory Influence of the Immunomodulator α-MSH.*" Immunology Today 18: 140–45, 1997. The α-, β-, and γ-MSH peptides are derived from post-translation processing and of the precursor protein pro-opiomelanocortin. Pro-opiomelanocortin is expressed in the pituitary gland, in two brain nuclei, and in several peripheral tissues. Effects of melanocortins have been described on behavior, metabolism, fever, inflammation, analgesia, addiction, nerve regeneration, and the cardiovascular system. The presence of the ancient anti-inflammatory peptide α-melanocyte-stimulating hormone [α-MSH (1–13), SYSMEHFRWGKPV] (SEQ. ID. NO. 13) in barrier organs, such as gut and skin, suggests a role in nonspecific, or innate, host defense.

α-MSH peptides significantly inhibit *S. aureus* colony formation and reverse the enhancing effect of urokinase on colony formation. α-MSH (SEQ. ID. NO. 13) antimicrobial effects occur over a broad range of concentrations, including the physiological (picomolar) range. Small concentrations of α-MSH peptides likewise reduce viability and germ tube formation of the yeast *C. albicans*.

Antimicrobial influences of α-MSH peptides could be mediated by their capacity to increase cellular cAMP. cAMP is significantly augmented in peptide-treated yeast. Reduced killing of pathogens is a detrimental consequence of therapy with anti-inflammatory drugs. Because α-MSH (SEQ. ID. NO. 13) has potent anti-inflammatory effects, its influence on *C. albicans* and *S. aureus* killing by human neutrophils has been determined. α-MSH peptides do not reduce killing, but rather enhance it, likely as a consequence of the direct antimicrobial activity. α-MSH peptides that combine anti-pyretic, anti-inflammatory, and antimicrobial effects may be useful in the treatment of disorders in which infection and inflammation coexist.

To improve the antimicrobial activity of this peptide, novel peptide analogs have been designed and synthesized and several modifications have been made. These analogs are referred to in this application as modified alpha-MSH peptides. In particular, the importance of the Proline amino acid has been evaluated and replaced with various amino acids.

In one preferred embodiment of the invention, a peptide is prepared that comprises R1-Lys-X1-Val (SEQ. ID. NO. 1), where Val is the carboxy-terminal amino acid and X1 is either Phe or DPhe and where R1 is His-Phe-Arg-Trp-Gly. In another preferred embodiment of the invention, a peptide is prepared that contains His-X2-Arg-Trp-Gly-Lys-Pro-Val (SEQ. ID. NO. 2), where X2 is, D-Phe, or DNa1. This can be combined with SEQ. ID NO. 1 via a Gly-Lys bond giving His-X2-Arg-Trp-Lys-X1-Val (SEQ. ID NO. 3). Here, the sequences are connected through a Gly-Lys peptide bond resulting in a peptide where Val is the carboxy-terminal amino acid.

In another preferred embodiment of the invention an octomeric peptide is prepared with a sequence R1-Lys-X3-Val (SEQ. ID NO. 4) wherein X3 is an amino acid bearing a non-polar functional group, and where Val is the carboxy-terminal amino acid. Non-polar functional group amino acids may be selected from the group consisting of Gly, Ala, Val, Leu, Ile, Met, Phe, Trp and their D-isomers thereof.

In another preferred embodiment of the invention, a peptide is prepared that comprises R1-Lys-Pro-X4 (SEQ. ID. NO. 5) where X4 is the carboxy-terminal amino acid and where X4 bears is an amino acid, not including Val, having a non-polar functional group, or a hydrophobic functional group. Hydrophobic functional group may be selected from the group consisting of Ala, DVal, Leu, Ile, Met, Pro, and their D-isomers thereof.

In another preferred embodiment of the invention, a peptide is prepared that comprises R1-X5-Pro-Val (SEQ. ID. NO. 6) wherein Val is the carboxy-terminal amino acid and where X5 is an amino acid, not including Lys, having a non-polar functional group.

In another preferred embodiment of the invention, a peptide is prepared that comprises R1-Lys-X6-Val (SEQ. ID. NO. 7) where Val is the carboxy-terminal amino acid and where X6 is an amino acid with a positively charged functional group. Positively charged functional group amino acids may be selected from the group consisting of Lys, Arg and their D-isomers thereof.

In another preferred embodiment of the invention, a peptide is prepared consisting of R1-Lys-X7-Val (SEQ. ID. NO. 8) where Val is the carboxy-terminal amino acid and where X7 is an amino acid having a negatively charged functional group. Negatively charged functional group amino acids may be selected from the group consisting of Asp, Glu, and their D-isomers thereof. In another preferred embodiment of the invention, a peptide is prepared where SEQ. ID NO. 2, His-X2-Arg-Trp-Gly is connected to the Lys of SEQ. ID NO. 8, giving His-X2-Arg-Trp-Gly-Lys-X7-Val (SEQ. ID. NO. 9), and where X2, as above, is DPhe or DNa1. Similar to above, SEQ. ID NO. 2 and SEQ. ID NO. 7 are connected via a Gly-Lys. In other words, SEQ. ID NO. 2 replaces the R1 in SEQ. ID NO. 7.

In another preferred embodiment of the invention, a peptide is prepared comprising DTrp in position 4 giving His-Phe-Arg-DTrp-Gly-Lys-Pro-Val. (SEQ. ID. NO. 10) where Val is the carboxy-terminal amino acid.

In another preferred embodiment of the invention, a peptide is prepared comprising R1-Lys-X8-Val (SEQ. ID. NO. 11) where Val is the carboxy-terminal amino acid and where X8 is an uncharged functional group polar amino acid. Uncharged functional group amino acids may be selected from the group consisting of Asn, Gln, Ser, Thr and their D-isomers thereof.

In another embodiment, a peptide is prepared comprising His-X2-Arg-Trp-Gly (SEQ. ID. NO. 2) connected through a Gly-Lys bond to R1-Lys-X8-Val (SEQ. ID. NO. 11) yielding His-X2-Arg-Trp-Gly-Lys-X8-Val (SEQ. ID NO. 12), again, where X8 is an amino acid with uncharged polar functional group and where Val is the carboxy-terminal amino acid. In other words, SEQ. ID NO. 2 has replaced the R1 in SEQ. ID NO. 11.

Peptides may be prepared in this invention with the techniques disclosed below. It is contemplated that each modified alpha-MSH peptide may be protected at the C-terminus and N-terminus with protecting groups known in the art such as C-amidation and N-acylation.

GENERAL DESCRIPTION OF THE INVENTION

The references cited above and below are incorporated by reference as if fully set forth herein. The current invention is directed to novel modified α-MSH peptides that have use in antimicrobial therapy. The invention maintains advantages over other antimicrobial therapy in that it is less likely to generate resistant microbial strains, maintains balance between strains of bacteria while helping to combat infection and it is virtually non-toxic to mammalian cells. Bacterial, parasitic, viral and fungal infections are contemplated.

To improve the antimicrobial activity of the naturally occurring α-MSH peptide, novel peptide analogs have been designed and synthesized and several novel modifications have been made.

Unmodified α-MSH (SEQ. ID. NO. 13) is an ancient, thirteen amino-acid peptide produced by post-translational processing of the larger precursor molecule propiomelanocortin. It shares the same 1–13 amino acid sequence with adrenocorticotropic hormone ("ACTH") (SEQ. ID. NO. 14), also derived from propiomelanocortin. α-MSH (SEQ. ID. NO. 13) is secreted by many cell types, including pituitary cells, monocytes, melanocytes, and keratinocytes. It can be found in the skin of rats, in the human epidermis, or in the mucosal barrier of the gastrointestinal tract in intact and hypophysectomized rats. See e.g. Eberle, A. N., "*The Melanotrophins*," Karger, Basel, Switzerland (1998); Lipton, J. M., et. al., "*Anti-inflammatory Influence of the Neuroimmunomodulator α-MSH*," Immunol. Today 18, 140–145 (1997); Thody, A. J., et. al., "*MSH Peptides are Present in Mammalian Skin*," Peptides 4, 813–815 (1983); Fox, J. A., et. al., "*Immunoreactive α-Melanocyte Stimulating Hormone, Its Distribution in the Gastrointestinal Tract of Intact and Hypophysectomized Rats*," Life. Sci. 18, 2127–2132 (1981).

α-MSH (SEQ. ID. NO. 13) and its derivatives are known to have potent antipyretic and anti-inflammatory properties, yet they have extremely low toxicity. They can reduce production of host cells' pro-inflammatory mediators in vitro, and can also reduce production of local and systemic reactions in animal models for inflammation. The "core" α-MSH sequence Met-Glu-His-Phe-Arg-Trp-Gly (SEQ. ID. NO. 14), for example, has learning and memory behavioral effects but little antipyretic and anti-inflammatory activity. In contrast, the active message sequence for the antipyretic and anti-inflammatory activities resides in the carboxy-terminal amino-acid lys-pro-val (SEQ. ID. NO. 15) sequence of α-MSH. This tripeptide has activities in vitro and in vivo that parallel but are more potent than those of the parent molecule. The anti-inflammatory activity of α-MSH (SEQ. ID. NO. 13) and/or its derivatives are disclosed in the following two patents which are hereby incorporated by reference: U.S. Pat. No. 5,028,592, issued on Jul. 2, 1991 to Lipton, J. M., entitled "ANTIPYRETIC AND ANTI-INFLAMMATORY LYS PRO VAL COMPOSITIONS AND METHOD OF USE;" U.S. Pat. No. 5,157,023, issued on Oct. 20, 1992 to Lipton, J. M., entitled "ANTIPREYTIC AND ANTI-INFLAMMATORY LYS PRO VAL COMPOSITIONS AND METHOD OF USE;" see also Catania, A., et. al., "*α-Melanocyte Stimulating Hormone in the Modulation of Host Reactions*," Endocr. Rev. 14, 564–576 (1993);

Lipton, J. M., et. al., "*Anti-inflammatory Influence of the Neuroimmunomodulator of α-MSH, Immunol.*" Today 18, 140–145 (1997); Rajora, N., et. al., "*α-MSH Production Receptors and Influence on Neopterin, in a Human Monocyte/macrophage Cell*" Line, J. Leukoc. Biol. 59, 248–253 (1996); Star, R. A., et. al., "*Evidence of Autocrine Modulation of Macrophage Nitric Oxide Synthase by α-MSH,*" Proc. Nat'l. Acad. Sci. (USA) 92, 8016–8020 (1995); Lipton, J. M., et. al., "*Anti-inflammatory Effects of the Neuropeptide α-MSH in Acute Chronic and Systemic inflammation,*" Ann. N.Y. Acad. Sci. 741, 137–148 (1994); Rajora, N., et. al., "*α-MSH Modulates Local and Circulating tumor Necrosis Factor a in Experimental Brain Inflammation,*" J. Neurosci, 17, 2181–2186 (1997); Richards, D. B., et. al., "*Effect of α-MSH (11–13) (lysine-proline-valine) on Fever in the Rabbit,*" Peptides 5, 815–817 (1984); Hiltz, M. E., et. al., "*Anti-inflammatory Activity of a COOH-terminal Fragment of the Neuropeptide α-MSH,*" FASEB J. 3, 2282–2284 (1989).

In addition to its anti-inflammatory and anti-pyretic function, a preferred aspect of the present invention involves the anti-microbial or anti-infection activity of the modified α-MSH-related peptides and/or their derivatives. As described below, modified α-MSH peptides have significant anti-infection uses.

Infections are not confined to a single cause. Multiple organisms and infectious agents, including bacteria, fungi, viruses and parasites, individually or in combination, can cause infection. For treatment of these infections, the novel α-MSH peptides may be applied locally to the site of the infection and/or inflammation by methods known in the art. For example, modified α-MSH peptides and their derivatives may be dissolved in solutions such as phosphate buffer saline, hyalurinate, methylcellulose, carboxymethlcellulose, or ethanol. Solvated α-MSH peptides may then be combined with vehicles such as injectable solutions, tables, capsules, topical ointments, creams, gels, aerosol sprays, suppositories, liquid solutions and absorbent materials.

For parenteral administration, the therapeutic peptides will be mixed in a composition with a non-toxic, biologically compatible carrier prior to administration. Usually, this will be an aqueous solution; such as normal saline or phosphate-buffered saline (PBS), Ringer's solution, Ringer's lactate or any isotonic physiologically acceptable solution for administration by the chosen means. Preferably, the solution is manufactured and packaged under current Good Manufacturing Processes (GMP's) as approved by the FDA.

In one embodiment of the above invention, modified α-MSH-related peptides are administered orally. Each oral composition according to the present invention may additionally comprise inert constituents including biologically compatible carriers, dilutents, fillers, wetting agents, suspending agents, solubilizing or emulsifying agents, salts, flavoring agents, sweeteners, aroma ingredients or combinations thereof, as is well-known in the art. Liquid dosage forms may include a liposome solution containing the liquid dosage form. As known by those ordinarily skilled in the art, suitable forms for suspending liposomes include emulsions, pastes, granules, compact or instantized powders, suspensions, solutions, syrups, and elixirs containing inert dilutents, such as purified water.

Tablets or capsules may be formulated in accordance with conventional procedures employing biologically compatible solid carriers well known in the art. For example, a pharmaceutical preparation may contain the composition dissolved in the form of a starch capsule, or hard or soft gelatin capsule which is coated with one or several polymer films, in accordance with U.S. Pat. No. 6,204,243 which is fully incorporated as if fully set out herein. The choice and usage of appropriate polymers, including additional materials such as softeners and pore-forming agents, control the site of dissolution of the capsule and the release of solution containing the active agent.

Preparation of the composition may also include dissolving the composition in a solvent, which is suitable for encapsulation into starch or gelatin capsules, or in a mixture of several solvents and, optionally, solubilizers and/or other excipients. The solution is then filled into starch capsules, or hard or soft gelatin capsules in a measured dose, the capsules are sealed, and the capsules are coated with a solution or dispersion of a polymer or polymer mixture and dried. The coating procedure may be repeated once or several times.

The solvents that are appropriate for dissolving the active agent are those that are biologically compatible with the host subject and in which the composition dissolves. Examples of these are ethanol, 1,2-propylene glycol, glycerol, polyethylene glycol 300/400, benzyl alcohol, medium-chained triglycerides and vegetable oils.

Medicament excipients may be added to the solution. Examples of such excipients are mono and/or di-fatty acid glycerides, sorbitan fatty acid esters, polysorbates, lecithin, sodium lauryl sulphate, sodium dioctylsulphosuccinate, aerosol and water-soluble cellulose derivatives. Mixtures of solvents and excipients may also be used. The soft or hard gelatin capsule may be coated with one or several polymer films, whereby the targeted capsule dissolution and release of the therapeutically effective composition is achieved through the film composition. The polymer or a mixture of polymers is dissolved or dispersed in an organic solvent or in a solvent mixture. For example, solvents include ethanol, isopropanol, n-propanol, acetone, ethyl acetate, methyl ethyl ketone, methanol, methylene chloride, propylene glycol monomethyl ether and water. See, in general, Remingtons's Pharmaceutical Sciences (18$^{th}$ Ed. Mack Publishing Co. 1990).

The properties of the polymer films may be further influenced by additions of pore-forming agents and softeners. Suitable pore-forming agents to form open pores, and thus to increase the diffusion rate through the polymer coating, are water-soluble substances, including lactose, saccharose, sorbitol, mannitol, glycerol, polyethylene glycol, 1,2-propylene glycol, hydroxypropyl cellulose, hydroxypropyl methylcellulose, methylcellulose, as well as mixtures thereof. Softeners include alkyl esters of citric acid, tartaric acid and 1,8-octanedi-carboxylic acid, triethyl citrate, tributyl citrate, acetyl triethyl citrate, dibutyl tartrate, diethyl sebacate, dimethyl phthalate, diethyl phthalate, dioctyl phthalate, castor oil, sesame oil, acetylated fatty acid glycerides, glycerol triacetate, glycerol diacetate, glycerol, 1,2-propylene glycol, polyethylene glycols and polyoxyethylene-polypropylene block copolymers, PEG-400 stearate, sorbitan mono-oleate, and PEG-sorbitan mono-oleate.

When administration is parenteral, injectable pharmaceuticals may be prepared in conventional forms, as aqueous or non-aqueous solutions or suspensions; as solid forms suitable for solution or suspension in liquid prior to injection; or as emulsions. Examples of non-aqueous solvents are propylene glycol, polyethylene glycol, vegetable oils such as olive oil, and injectable organic esters such as ethyl oleate. Examples of suitable excipients are water, saline, dextrose, mannitol, lactose, lecithin, albumin, sodium glutamate, cysteine hydrochloride, or the like. In addition, the injectable pharmaceutical compositions may contain minor amounts of non-toxic auxiliary substances, such as wetting agents, pH buffering agents, and the like. If desired, absorption-enhancing preparations (e.g., liposomes) may be utilized.

The therapeutic may be administered to the subject in a single administration, or it may be administered in a series of administrations. A lower concentration of the therapeutic over a long period of time may be most effective, or a higher concentration over a short period of time may be preferred. Using ordinary skill, the competent clinician will be able to optimize the dosage of a particular therapeutic composition in the course of routine clinical trials.

The following examples demonstrate the ability and application of α-MSH related peptides to combat bacteria. Methods in microbiology, molecular biology, and cell culture used but not explicitly described in this disclosure have already been amply reported in the scientific literature. The peptides used in the following examples were prepared by solid-phase peptide synthesis and purified by reversed phased high performance liquid chromatography.

Statistical significance disclosed in the examples below may be analyzed using one-way analysis of variance and the Student's t test. Probability values greater than 0.05 were considered significant.

EXAMPLE I

Anti-Fungal Properties of α-MSH Related Peptides Against *Candida albicans*

Clinical isolates of *C. albicans* were also obtained from the collection of the Department of Microbiology, Ospedale Maggiore di Milano. Cultures of *C. albicans* were maintained on Sabouraud's agar slants and periodically transferred to Sabouraud's agar plates and incubated for 48 hours at 28° C. To prepare stationary growth-phase yeast, a colony may be taken from the agar plate, transferred into 30 ml of Sabouraud-dextrose broth, and incubated for 72 hours at 32° C. Cells were centrifuged at 1000×g for ten minutes, and the pellet may be washed twice with distilled water. Cells were counted and suspended in Hank's balanced salt solution ("HBSS") to the desired concentration. Viability, determined by exclusion of 0.01% methylene blue, remained greater than 98%.

At $1\times10^6$/ml in HBSS, these fungi were incubated in the presence or absence of modified α-MSH peptides at concentrations ranging from $10^{-15}$ to $10^{-4}$ M for two hours at 37° C. Cells were then washed in cold distilled water and diluted with HBSS to a concentration of 100 organisms/ml. One-milliliter aliquots were then dispensed on blood agar plates and incubated for 48 hours at 37° C. The organism's viability may be estimated from the number of colonies formed.

FIG. 1 shows that modified α-MSH peptides greatly reduced the ability of *C. albicans* to form colonies. This demonstrates that modified α-MSH peptides can inhibit the growth of *Candida albicans*, an agent known to cause candidiasis, vaginitis, urethritis, balanoposthitis, and gastrointestinal infection in cancer patients. Bast, R., et al., "Cancer Medicine," BC Decker, Inc., p. 157–163, 2000.

The modified α-MSH peptides not only retain their effectiveness, they, unexpectedly, are more potent inhibitors of *C. albicans* growth relative to naturally occurring α-MSH (SEQ. ID. NO. 13), which inhibited less than 80% of the colonies. See U.S. patent application Ser. No. 09/535,066. Applicants have designed and evaluated the antimicrobial activity of modified α-MSH peptides toward *C. albicans*. These peptides were designed to determine the effect of sequence Lys-Pro-Val (SEQ. ID. NO. 15) on biological activity. The minimally active His-Phe-Arg-Trp (SEQ. ID. NO. 16) sequence was chosen. This sequence is important in interacting with melanocortin receptors, while the Lys-Pro-Val (SEQ. ID. NO. 15) sequence is known to be important for antimicrobial activity. In an attempt to elucidate the contributions of each of the amino acids of the Lys-Pro-Val (SEQ. ID. NO. 15) sequence toward antimicrobial activity, an alanine scan was performed. As shown in Table 1, the alanine substitutions displayed that Lys and Pro are more important than Val in activity. In contrast, replacing Val with DVal, and with Leu, did not substantially alter antimicrobial activity, showing that this residue is not crucial. The importance of Val in the Lys-Pro-Val (SEQ. ID. NO. 15) sequence is therefore unclear, and it could be a remnant of pro-opiomelanocortin biosynthesis.

Replacing the Phe residue within the His-Phe-Arg sequence with DNa1 (SEQ. ID. NO. 22) resulted in increased activity in almost all peptides tested, confirming a behavior found previously in melanocortin peptides.

No substantial modification in activity was shown by SEQ. ID. NO. 30 and SEQ. ID. NO. 31, where Ser replaced the Pro residue in the Lys-Pro-Val sequence. Replacing the Pro residue from the Lys-Pro-Val sequence with either Asp (SEQ. ID. NO. 41) or Glu (SEQ. ID. NO. 43), resulted in decreased activity. This result confirms earlier studies demonstrating that a negative charge in the carboxy-terminal region is deleterious for antimicrobial activity of melanocortin peptides.

Peptides bearing a replacement of the Pro residue from the Lys-Pro-Val sequence with either Phe (SEQ. ID. NO. 36) or DPhe (SEQ. ID. NO. 37), exhibited potent antimicrobial activity toward *Candida albicans*.

This result indicates that the anticandidacidal activity of the peptide may be affected by enhancing carboxy-terminal hydrophobicity without modifying the net charge of the peptide (+2). Many structure parameters such as net positive charge, hydrophobicity, peptide helicity, hydrophobic moment, and the size of peptide influence the activity and selectivity of membrane-active peptides.

For example, (SEQ. ID. NO. 36), which contains enhanced hydrophobicity but unaltered net charge, showed remarkable anticandidacidal activity suggesting that its mechanism of action is different from that of other antimicrobial peptides. Most other antimicrobial peptides alter membrane permeability and impair internal homeostasis of the organism. No evidence suggests that α-MSH (SEQ. ID. NO. 13) and its analogues operate in this way. Because the overall positive charge of α-MSH peptides is very low relative to other antimicrobial peptides, it appears the positive charge alone does not account for the antimicrobial activity.

Recent reports indicate that the candidacidal effect of α-MSH is mediated through cAMP induction. Catania, A., et al., "*Antimicrobial Effects of α-MSH Peptides*," Journal of Leukocyte Biology 67: 233–239, 2000. It is likely, therefore, that the modified α-MSH-related peptides enhance intracellular cAMP levels and thereby induced toxicity.

EXAMPLE II

Generation of a Modified α-MSH Peptide

This example illustrates the generation of a novel peptide by modifying an α-MSH peptide (SEQ. ID. NO. 13). Peptide No. 20 is chosen here for this example. This is a representative example of how all of the peptide sequences in Table 1 were created. By adding the desired amino acids during synthesis of the growing peptide chain, each of the peptide sequences can be generated. All peptides were synthesized by solid-phase peptide synthesis followed by RP-HPLC purification.

The peptides were synthesized on 0.15 g of Wang resin (substitution 0.7 mmol/g) by manual methods using $N^\alpha$-Fmoc chemistry and an orthogonal side chain protection strategy. The entire synthesis was performed under an argon atmosphere. The resin was swollen in DCM/DMF (1:1) for 2 hours. To generate peptide SEQ. ID. NO. 36, the following amino acids were added by stepwise addition: Fmoc-His ($N^{im}$-Trt)-OH, $N^\alpha$-Fmoc-DNa1-OH, $N^\alpha$-Fmoc-Arg($N^g$-Pbf)-OH, $N^\alpha$-Fmoc-Trp $N^\alpha$-Fmoc-Gly-OH, $N^\alpha$-Fmoc-Lys-OH, $N^\alpha$-Fmoc-Phe-OH, $N^\alpha$-Fmoc-Val-OH, using standard solid phase methods. Each coupling reaction was achieved using a 3-fold excess each of the amino acids, HBTU, and HOBt in the presence of a 6-fold excess of DIPEA for 1 h. Deprotection of the $N^\alpha$-Fmoc group was carried out by treating the protected peptide resin with 25% piperidine solution in DMF (1×4 mL, 5 min., 1×4 mL, 20 min). After each coupling and deprotection, the peptide resin was washed with DMF (3×4 mL), DCM (3×50 mL) and then again with DMF. The peptide sequences were thus assembled by alternate cycles of coupling and de-protection. After coupling of the carboxy-terminal amino acid, the amino-terminal Fmoc group was de-blocked as before and after the peptide-resin was thoroughly washed with DCM (4×25 mL) and dried under an argon atmosphere to yield dried peptide-resin.

The peptide was cleaved from the resin by treatment with 4 mL of $Et_3SiH$ (5%), water (5%), p-thiocresol/p-cresol (0.1%, 1:1) in TFA with shaking at room temperature for 3 hours. The resin was then removed from the solution (containing the cleaved peptide) by filtration and the crude peptide was recovered by precipitation with cold anhydrous ethyl ether. Centrifugation at 2000 rpm for 3 minutes followed by decantation of the ether supernatant and air-drying of the residue to yield the crude peptide as a white to pale beige colored amorphous solid.

Final peptide purification was achieved using a preparative RP-HPLC Vydac C18 (218TP1520, 15 μm). The peptides were injected onto the column at a concentration of 20–30 mg/mL in 20% aqueous $CH_3CN$. They were eluted with a $CH_3CN$ gradient (0 to 55%) over 35 minutes at a flow rate of 15.0 mL/min, with a constant concentration of TFA (0.1% v/v). The separations were monitored at 230 nm and 280 nm and integrated with a Shimadzu diode array detector (SPD-M10A VP dual wavelength absorbency detector model UV-D). Fractions corresponding to the major peak were collected, pooled, and lyophilized to yield the final peptides as pure (>95%) white solids. Amino acid analyses were carried out using a Pico-Tag Work Station. Lyophilized samples of peptides (50–1000 pmol) were hydrolyzed in heat-treated borosilicate tubes (4×50 mm) using the Pico-Tag Work Station (Waters-Millipore, Waltham, Mass.) for 1 hour at 150° C. with 200 ml 6 N HCl containing 1% phenol; a Pico-Tag column (3.9×15 mm) was employed to separate the amino acid derivatives. The analytical data for each compound is presented in Table 1.

From the foregoing, it will be appreciated that specific embodiments of the invention have been described herein for purposes of illustration, but that various modifications may be made without deviating from the spirit and scope of the invention. Accordingly, the invention is not limited except as by the appended claims. The preceding Examples are intended only as examples and are not intended to limit the invention. It is understood that modifying the examples above does not depart from the spirit of the invention. It is further understood that the each example may be applied on its own or in combination with other examples.

TABLE 1

Peptide sequences and inhibitory effect on Candida Albicans

| SEQ. ID. NO. | Structure | % Inhib. | SD |
|---|---|---|---|
| SEQ. ID. NO. 17 | His-Phe-Arg-Trp-Gly-Lys-Pro-*DVal* | 82.5 | 26.8 |
| SEQ. ID. NO. 18 | His-Phe-Arg-Trp-Gly-*Ala*-Pro-Val | 26.2 | 29.1 |
| SEQ. ID. NO. 19 | His-Phe-Arg-Trp-Gly-Lys-*Ala*-Val | 12.8 | 18.1 |
| SEQ. ID. NO. 20 | His-Phe-Arg-Trp-Gly-Lys-Pro-*Ala* | 68.4 | 31.5 |
| SEQ. ID. NO. 21 | His-*DPhe*-Arg-Trp-Gly-Lys-Pro-Val | 79.4 | 27.3 |
| SEQ. ID. NO. 22 | His-*DNal*-Arg-Trp-Gly-Lys-Pro-Val | 95.3 | 7.7 |
| SEQ. ID. NO. 23 | His-Phe-Arg-*DTrp*-Gly-Lys-Pro-Val | 81.9 | 24.5 |
| SEQ. ID. NO. 24 | His-Phe-Arg-Trp-Gly-Lys-Pro-*Leu* | 86.6 | 23.2 |
| SEQ. ID. NO. 25 | His-Phe-Arg-Trp-Gly-Lys-*DAla*-Val | 43.7 | 29.5 |
| SEQ. ID. NO. 26 | His-DNal-Arg-Trp-Gly-Lys-*Ala*-Val | 28.0 | 24.5 |
| SEQ. ID. NO. 27 | His-DNal-Arg-Trp-Gly-Lys-*DAla*-Val | 69.2 | 27.1 |
| SEQ. ID. NO. 28 | His-Phe-Arg-Trp-Gly-Lys-*Gly*-Val | 41.8 | 27.9 |
| SEQ. ID. NO. 29 | His-DNal-Arg-Trp-Gly-Lys-*Gly*-Val | 36.2 | 24.2 |
| SEQ. ID. NO. 30 | His-Phe-Arg-Trp-Gly-Lys-*Ser*-Val | 32.3 | 25.5 |
| SEQ. ID. NO. 31 | His-DNal-Arg-Trp-Gly-Lys-*Ser*-Val | 73.9 | 25.0 |

TABLE 1-continued

Peptide sequences and inhibitory effect on *Candida Albicans*

| SEQ. ID. NO. | Structure | % Inhib. | SD |
|---|---|---|---|
| SEQ. ID. NO. 32 | His-Phe-Arg-Trp-Gly-Lys-*Phe*-Val | 90.0 | 9.3 |
| SEQ. ID. NO. 33 | His-Phe-Arg-Trp-Gly-Lys-*DPhe*-Val | 97.5 | 4.2 |
| SEQ. ID. NO. 34 | His-DPhe-Arg-Trp-Gly-Lys-*Phe*-Val | 89.6 | 14.5 |
| SEQ. ID. NO. 35 | His-DPhe-Arg-Trp-Gly-Lys-*DPhe*-Val | 82.0 | 24.9 |
| SEQ. ID. NO. 36 | His-DNal-Arg-Trp-Gly-Lys-*Phe*-Val | 99.7 | 0.6 |
| SEQ. ID. NO. 37 | His-DNal-Arg-Trp-Gly-Lys-*DPhe*-Val | 57.6 | 26.7 |
| SEQ. ID. NO. 38 | His-Phe-Arg-Trp-Gly-Lys-*Asp*-Val | 5.9 | 9.1 |
| SEQ. ID. NO. 39 | His-Phe-Arg-Trp-Gly-Lys-*DAsp*-Val | 15.7 | 15.6 |
| SEQ. ID. NO. 40 | His-DPhe-Arg-Trp-Gly-Lys-*Asp*-Val | 3.7 | 4.9 |
| SEQ. ID. NO. 41 | His-DNal-Arg-Trp-Gly-Lys-*Asp*-Val | 16.8 | 22.3 |
| SEQ. ID. NO. 42 | His-Phe-Arg-Trp-Gly-Lys-*Glu*-Val | 11.2 | 12.7 |
| SEQ. ID. NO. 43 | His-DNal-Arg-Trp-Gly-Lys-*Glu*-Val | 32.3 | 25.6 |
| SEQ. ID. NO. 44 | His-Phe-Arg-Trp-Gly-Lys-*Lys*-Val | 41.0 | 26.9 |
| SEQ. ID. NO. 45 | His-DNal-Arg-Trp-Gly-Lys-*Lys*-Val | 85.4 | 26.1 |

What is claimed is:

1. An octomeric peptide comprising R1-Lys-X1-Val (SEQ. ID NO. 1), wherein X1 is Phe or DPhe, and R1 is His-Phe-Arg-Trp-Gly.

2. An octomeric peptide comprising R1-Lys-X3-Val (SEQ. ID NO. 4) sequence, wherein Val is the carboxy-terminal amino acid, R1 is His-Phe-Arg-Trp-Gly, and X3 is an amino acid having a non-polar functional group selected from the group consisting of Gly, Ala, Val, Leu, Ile, Met, Phe and Trp.

3. An octomeric peptide comprising His-Phe-Arg-Trp-Gly-Lys-Lys-Val (SEQ ID NO. 44).

4. An octomeric peptide comprising R1-Lys-Pro-X4 (SEQ. ID NO. 5) wherein X4 is an amino acid, not including Val, having a hydrophobic functional group or a non-polar functional group, and R1 is His-Phe-Arg-Trp-Gly.

5. The octomeric peptide of claim 4, wherein the amino acid having a hydrophobic functional group is selected from the group consisting of Ala, Leu, Ile, Met and Pro.

6. The octomeric peptide of claim 4, wherein the amino acid having a non polar functional group is selected from the group consisting of Gly, Ala, Pro, Leu, Ile, Met, Phe and Trp.

7. An octomeric peptide comprising R1-X5-Pro-Val (SEQ. ID NO. 6) wherein X5 is an amino acid having a non-polar functional group not including Lys, and R1 is His-Phe-Arg-Trp-Gly.

8. The octomeric peptide of claim 7, wherein the amino acid having a hydrophobic functional group is selected from the group consisting of Ala, Leu, Ile, Met and Pro.

9. An octomeric peptide comprising R1-Lys-X6-Val (SEQ. ID NO. 7) wherein X6 is selected from the group consisting of Lys and Arg, and R1 is His-Phe-Arg-Trp-Gly.

10. An octomeric peptide comprising R1-Lys-X7-Val (SEQ. ID NO. 8) wherein X7 is an amino acid having a negatively charged functional group, and R1 is His-Phe-Arg-Trp-Gly.

11. The peptide of claim 10, wherein the amino acid having a negatively charged functional group is selected from the group consisting of Asp and Glu.

12. An octomeric peptide comprising an amino acid sequence His-X1-Arg-Trp-Gly-Lys-X2-Val (SEQ. ID NO. 9), wherein X1 is DPhe, and X2 is an amino acid having a negatively charged functional group.

13. An octomeric peptide comprising R1-Lys-X8-Val (SEQ. ID NO. 11) wherein X8 is an amino acid having an uncharged polar functional group, and R1 is His-Phe-Arg-Trp-Gly.

14. The octomeric peptide of claim 13, wherein the amino acid having an uncharged polar functional group is selected from the group consisting of Asn, Gln, Ser and Thr.

* * * * *